United States Patent
Lee et al.

(10) Patent No.: US 9,540,234 B2
(45) Date of Patent: Jan. 10, 2017

(54) NANOGAP DEVICE AND METHOD OF PROCESSING SIGNAL FROM THE NANOGAP DEVICE

(71) Applicant: Samsung Electronics Co., Ltd., Suwon-Si, Gyeonggi-Do (KR)

(72) Inventors: Chang-seung Lee, Yongin-si (KR); Yong-sung Kim, Namyangju-si (KR); Jeo-young Shim, Yongin-si (KR); Joo-ho Lee, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 929 days.

(21) Appl. No.: 13/855,991

(22) Filed: Apr. 3, 2013

(65) Prior Publication Data

US 2014/0125322 A1 May 8, 2014

(30) Foreign Application Priority Data

Nov. 5, 2012 (KR) .................. 10-2012-0124463

(51) Int. Cl.
*G01N 33/487* (2006.01)
*B82Y 15/00* (2011.01)
*B82Y 99/00* (2011.01)

(52) U.S. Cl.
CPC ......... *B82Y 15/00* (2013.01); *G01N 33/48721* (2013.01); *B82Y 99/00* (2013.01)

(58) Field of Classification Search
CPC .. G01N 27/403; G01N 27/413; G01N 27/414; G01N 27/4035; G01N 27/4145; G01N 27/4146; G01N 27/4148; G01N 33/48721; H01L 29/413; H01L 29/1606; H01L 29/41733; B82Y 5/00

See application file for complete search history.

(56) References Cited

U.S. PATENT DOCUMENTS 8,828,138 B2 * 9/2014 Bedell .................... B82Y 15/00
117/2
9,030,187 B2 * 5/2015 Lee .................. G01N 33/48721
204/400

(Continued)

FOREIGN PATENT DOCUMENTS

JP 2007-278906 A 10/2007
JP 4873463 B2 2/2012

(Continued)

OTHER PUBLICATIONS

Xie, P. et al. "Local Electrical Potential Detection of DNA by Nanowire-nanopore Sensors" (2012) Nature Nanotechnology, vol. 7: 119-125.

*Primary Examiner* — Tucker J Wright
*Assistant Examiner* — Stephen C Smith
(74) *Attorney, Agent, or Firm* — Harness, Dickey & Pierce, P.L.C.

(57) ABSTRACT

A nanogap device which may include a first insulation layer having a nanopore formed therein, a first channel layer which may be on the first insulation layer, a first source electrode and a first drain electrode which may be respectively in contact with both ends of the first channel layer, a second insulation layer which may cover the first channel layer, the first source electrode, and the first drain electrode, and a first nanogap electrode which may be on the second insulation layer and may be divided into two parts with a nanogap, which faces the nanopore, interposed between the two parts.

22 Claims, 11 Drawing Sheets

(56) References Cited

U.S. PATENT DOCUMENTS

| | | | |
|---|---|---|---|
| 9,097,719 B2* | 8/2015 | Choi .................. | B82Y 15/00 |
| 2005/0167740 A1 | 8/2005 | Furukawa et al. | |
| 2006/0275778 A1* | 12/2006 | Wu .................. | G01N 33/48721 |
| | | | 435/6.11 |
| 2010/0066348 A1* | 3/2010 | Merz .................. | C12Q 1/6869 |
| | | | 324/71.1 |
| 2010/0327847 A1* | 12/2010 | Leiber .................. | B82Y 15/00 |
| | | | 324/71.1 |
| 2011/0279125 A1* | 11/2011 | Bedell .................. | B82Y 15/00 |
| | | | 324/444 |
| 2013/0069665 A1* | 3/2013 | Jaramillo-Botero ... | B82Y 15/00 |
| | | | 324/457 |

FOREIGN PATENT DOCUMENTS

| | | |
|---|---|---|
| KR | 10-2006-0081858 A | 7/2006 |
| KR | 10-0849384 B1 | 7/2008 |
| KR | 10-2009-0073396 A | 7/2009 |
| KR | 10-0988728 B1 | 10/2010 |
| KR | 10-2011-0018502 A | 2/2011 |
| KR | 10-1032067 B1 | 5/2011 |
| KR | 10-2011-0080229 A | 7/2011 |

* cited by examiner

NANOGAP DEVICE AND METHOD OF PROCESSING SIGNAL FROM THE NANOGAP DEVICE

CROSS-REFERENCE TO RELATED APPLICATIONS

This application claims priority under 35 U.S.C. §119 to Korean Patent Application No. 10-2012-0124463, filed on Nov. 5, 2012, in the Korean Intellectual Property Office, the disclosures of which are incorporated herein in their entirety by reference.

BACKGROUND

1. Field

Example embodiments relate to a nanogap device, a signal processing method using the nanogap device, and/or a method of manufacturing the nanogap device.

2. Description of the Related Art

Various methods have been developed to detect a target biomolecule such as a DNA (deoxyribonucleic acid) from a sample. Among them, a method using a nanogap has been identified as a DNA detection system.

At present, a system for measuring a tunneling current or a blockade current when a DNA, a ribonucleic acid (RNA), or the like passes through a nanogap has been implemented variously. Signal detection may be difficult because a molecule may pass through a nanogap quickly and a signal from the nanogap is small. For example, since DNA may move at an ultrahigh speed of 107 base/sec or higher, existing electrical signal detecting methods may have difficulty in distinguishing four different DNA bases having an interval of 0.37 nm.

SUMMARY

Example embodiments relate to nanogap devices and/or signal processing methods using the nanogap devices.

Additional aspects will be set forth in part in the description which follows and, in part, will be apparent from the description, or may be learned by practice of example embodiments.

According to example embodiments, a nanogap device includes a first insulation layer having a nanopore formed therein, a first channel layer formed on the first insulation layer, a first source electrode and a first drain electrode respectively formed in contact with both ends of the first channel layer, a second insulation layer which covers the first channel layer, the first source electrode, and the first drain electrode, and a first nanogap electrode which may be formed on the second insulation layer and may be divided into two parts with a nanogap, which faces the nanopore, interposed between the two parts.

In example embodiments, the first nanogap electrode may serve as a gate electrode with respect to the first channel layer.

In example embodiments, portions of the two parts of the first nanogap electrode that face the nanogap may be narrower than the other portions.

In example embodiments, a thickness of the first nanogap electrode may be 1 nm or less.

In example embodiments, a length of the nanogap of the first nanogap electrode may be 2 nm or less.

In example embodiments, the first nanogap electrode may include a graphene material.

In example embodiments, the nanogap device may further include a first protection layer which may be formed on the first nanogap electrode, a second nanogap electrode which may be formed on the first protection layer and may be divided into two parts with a nanogap, which faces the nanopore, interposed between the two parts, a third insulation layer which may be formed on the second nanogap electrode, a second channel layer which may be formed on the third insulation layer, and a second source electrode and a second drain electrode respectively which may be formed in contact with both ends of the second channel layer.

In example embodiments, the second nanogap electrode may serve as a gate electrode with respect to the second channel layer.

In example embodiments, the nanogap device may further include a second protection layer which may cover the second channel layer, the second drain electrode, and the second source electrode.

In example embodiments, portions of the two parts of the second nanogap electrode that face the nanogap may be narrower than the other portions.

In example embodiments, a thickness of the second nanogap electrode may be 1 nm or less.

In example embodiments, a length of the nanogap of the second nanogap electrode may be 2 nm or less.

In example embodiments, the second nanogap electrode may include a graphene material.

In example embodiments, the nanogap device may further include a substrate which may have a hole formed therein, and the first insulation layer may be formed on the substrate so that the nanopore may face the hole of the substrate.

In example embodiments, the hole may have an inclined side surface and may narrow from an entrance to an inside of the hole.

According to example embodiments, a method of processing a signal from a nanogap device may include arranging a plurality of the above-described nanogap devices such that respective nanogaps of the nanogap devices may face one another, measuring a drain current signal between the first drain electrode and the first source electrode of each of the nanogap devices according to time, and synchronizing the respective drain current signals of the nanogap devices with one another.

In example embodiments, the method may further include summing the synchronized drain current signals of the nanogap devices to obtain an amplification signal, or obtaining an error signal from a difference between the synchronized drain current signals of the nanogap devices.

According to example embodiments, a method of processing a signal from the above-described nanogap device may include measuring a first drain current signal between the first drain electrode and the first source electrode according to time, and measuring a second drain current signal between the second drain electrode and the second source electrode according to time.

In example embodiments, the method may further include synchronizing the first drain current signal with the second drain current signal. The method may further include obtaining an amplification signal from a sum of the synchronized first and second drain current signals, or obtaining an error signal from a difference between the synchronized first and second drain current signals.

BRIEF DESCRIPTION OF THE DRAWINGS

The above and other features and advantages of example embodiments will become apparent by describing in detail example embodiments with reference to the attached drawings. The accompanying drawings are intended to depict example embodiments and should not be interpreted to limit the intended scope of the claims. The accompanying drawings are not to be considered as drawn to scale unless explicitly noted.

DETAILED DESCRIPTION

Figure 1:
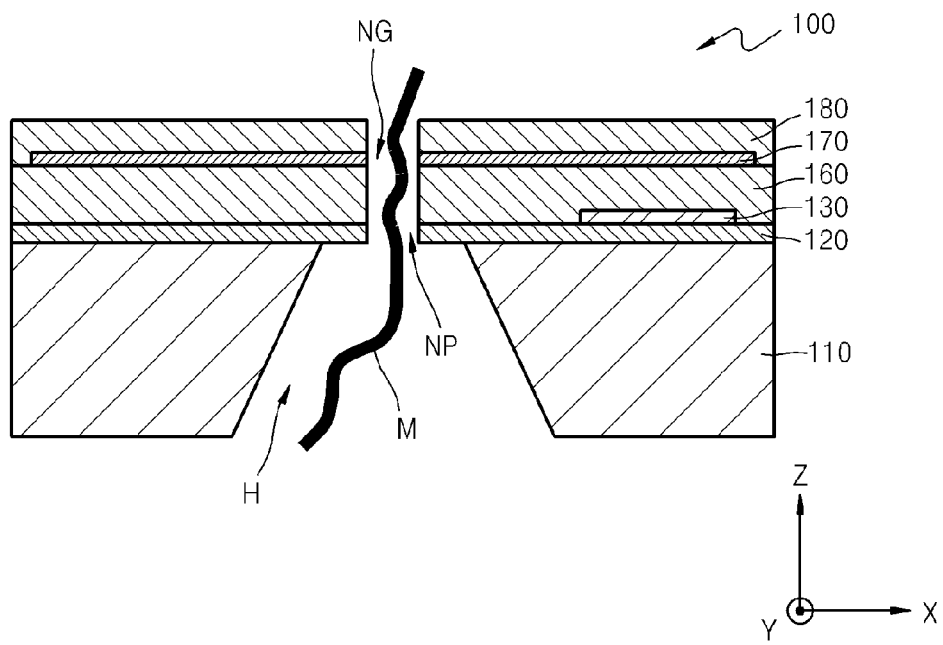
FIG. 1 is a cross-sectional view of a nanogap device according to example embodiments.

Example embodiments will now be described more fully with reference to the accompanying drawings, in which some example embodiments are shown. Example embodiments may, however be embodied in many different forms and should not be construed as being limited to the embodiments set forth herein; rather, these example embodiments are provided so that this disclosure will be thorough and complete, and will fully convey the scope of example embodiments of inventive concepts to those of ordinary skill in the art. In the drawings, the thicknesses of layers and regions are exaggerated for clarity. Like reference numerals in the drawings denote like elements, and thus their description may be omitted.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements or layers should be interpreted in a like fashion (e.g., "between" versus "directly between," "adjacent" versus "directly adjacent," "on" versus "directly on". As used herein the term "and/or" includes any and all combinations of one or more of the associated listed items. Expressions such as "at least one of," when preceding a list of elements, modify the entire list of elements and do not modify the individual elements of the list.

It will be understood that, although the terms "first," "second," etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be orientated "above" the other elements or features. Thus, the exemplary term "below" can encompass both an orientation of above and below. The device may be otherwise orientated (rotated 90 degrees or at other orientations) and the spatially relative descriptors used herein interpreted accordingly.

The terminology used herein is for the purpose of describing particular embodiments only and is not intended to limit example embodiments. As used herein, the singular forms "a," "an" and "the" are intended to include the plural forms as well, unless the context clearly indicates otherwise. It will be further understood that the terms "comprises" and/or "comprising," when sued in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as being limited to the particular shapes of regions illustrated herein and are to include deviations in shapes that result, for example, from manufacturing. For example, an implanted region illustrated as a rectangle will have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Hereinafter, a nanogap device, a signal processing method using the nanogap device, and a method of manufacturing the nanogap device according to example embodiments will be described more fully with reference to the accompanying drawings.

Figure 2:
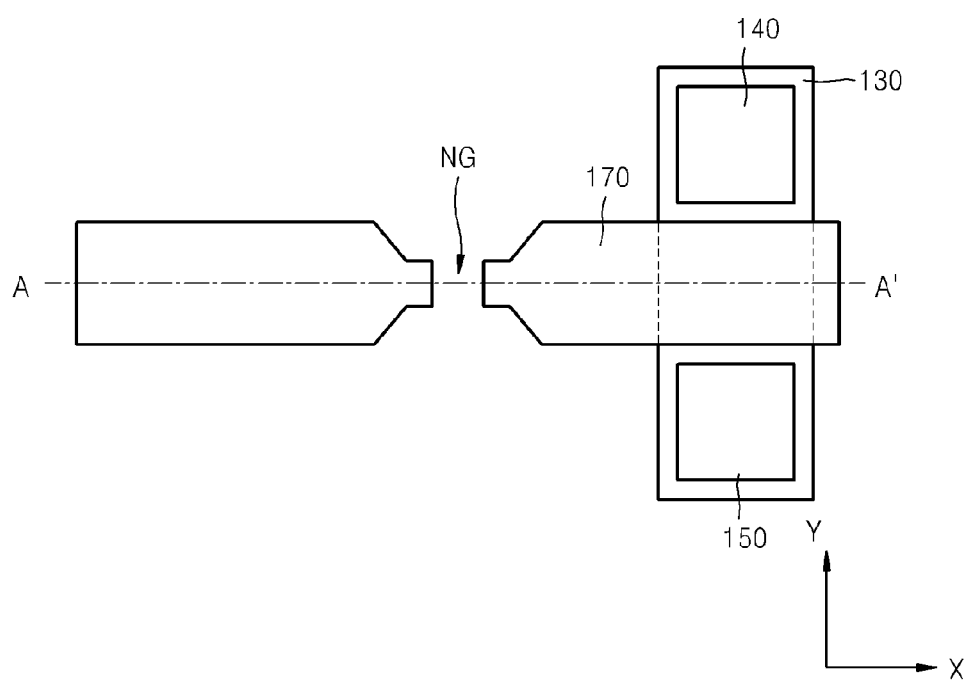
FIG. 2 is a plan view of an arrangement of a first nanogap electrode, a first drain electrode, and a first source electrode of the nanogap device of FIG. 1.

FIG. 1 is a cross-sectional view of a nanogap device 100 according to example embodiments, and FIG. 2 is a plan view of an arrangement of a first nanogap electrode 170, a first drain electrode 140, and a first source electrode 150 of the nanogap device 100 of FIG. 1.

Referring to FIGS. 1 and 2, the nanogap device 100 may include a first insulation layer 120 which may have a nanopore NP, a first channel layer 130 which may be formed on the first insulation layer 120, a first drain electrode 140 and a first source electrode 150 which may be respectively formed on both ends of the first channel layer 130 to contact the both ends, a second insulation layer 160 that may cover the first channel layer 130, the first drain electrode 140, and the first source electrode 150, and a first nanogap electrode 170 that may be formed on the second insulation layer 160 and may be divided into two parts with a nanogap NG which may face the nanopore NP there between.

When a target molecule M, for example, a deoxyribonucleic acid (DNA), passes through the nanogap NG, the nanogap device 100 may generate a signal for distinguishing bases that may constitute the DNA. According to the present embodiment, the nanogap device 100 may have a structure that may enable the first nanogap electrode 170 to be used as a gate electrode of a transistor.

A structure and materials of the nanogap device 100 will now be described in detail.

A substrate 110 may be disposed to support the first insulation layer 120, the first channel layer 130 which may be formed on the first insulation layer 120, and the first nanogap electrode 170, and may have a hole H that may face the nanopore NP which may be formed in the first insulation layer 120. The substrate 110 may be formed of a semiconductor material, a polymer material, or the like. Examples of the semiconductor material may include silicon (Si), germanium (Ge), gallium arsenide (GaAs), and/or gallium nitride (GaN), and examples of the polymer material may include an organic polymer and/or an inorganic polymer. The substrate 110 may be formed of quartz, glass, or the like. The hole H which may be formed in the substrate 110 may have a size of several μm or less, may have an inclined side surface, and/or may have a shape that narrows from its entrance to the inside. The hole H having this shape may guide the target molecule M so that the target molecule M may easily flow from the bottom of the substrate 110 toward the nanogap NG.

The first insulation layer 120 may be formed of an insulation material, for example, silicon nitride or silicon oxide. For example, SiO2, HfO2, Al2O3, Si3N4, or any mixtures thereof may be used. Alternatively, the first insulation layer 120 may be a multi-layered film including multiple layers respectively formed of the aforementioned materials. The nanopore NP formed in the first insulation layer 120 may be connected to the hole H of the substrate 110. In other words, the nanopore NP may be located to face the hole H. The size of the nanopore NP may be determined in consideration of the size of the target molecule M, which is to be detected. The nanopore NP may be formed using focused ion beam (FIB) equipment.

The first channel layer 130 may be formed of any of various sorts of semiconductor materials. Examples of the semiconductor materials may include Si, Ge, a compound semiconductor, such as GaAs or GaN, and/or an oxide semiconductor, such as, zinc oxide (ZnO), indium (InO), tin oxide (SnO), indium zinc oxide (InZnO), zinc tin oxide (ZnSnO), or indium tin oxide (InSnO). The first channel layer 130 may be mono-layered or multi-layered.

The first drain electrode 140 and the first source electrode 150 may be respectively formed on both ends of the first channel layer 130 to contact the both ends, and may be formed of a metal material having high electrical conductivity, for example, platinum (Pt), ruthenium (Ru), gold (Au), silver (Ag), molybdenum (Mo), aluminum (Al), tungsten (W), or copper (Cu).

The second insulation layer 160 may be formed of an insulation material, for example, silicon nitride or silicon oxide. For example, SiO2, HfO2, Al2O3, Si3N4, or any mixtures thereof may be used. Since the first nanogap electrode 170, which may be formed on the second insulation layer 160, may serve as a gate electrode, the second insulation layer 160 may serve as a gate insulation layer. Accordingly, as the second insulation layer 160 becomes thinner, a small change of a gate voltage may be amplified well. The second insulation layer 160 may be formed to have a thickness in the range of about 5 nm to about 20 nm. Here, the thickness of the second insulation layer 160 may denote a distance from an upper surface of the first channel layer 130 and a lower surface of the first nanogap electrode 170.

The first nanogap electrode 170 may be formed of a metal material having high conductivity. The first nanogap electrode 170 may be formed to have a similar thickness to a DNA base, for example, a thickness of about 1 nm or less. The first nanogap electrode 170 may be formed of a graphene material. Graphene is a hexagonal mono-layered structure formed of carbon, and the mobility of charge within graphene is high. Thus, graphene may show similar behavior as a metal having high electrical conductivity. Moreover, the thickness of graphene may be thin, namely, several Å, and thus it may be easy to obtain a nano-sized nanogap capable of measuring a tunneling current change caused by the target molecule M passing through the nanogap NG. The first nanogap electrode 170 may be divided into the two parts having the nanogap NG therebetween, and the width of a portion of the first nanogap electrode 170 that may face the nanogap NG may be less than that of the other portions thereof. This shape may facilitate formation of a small nanogap NG which may have a size of several nanometers. The nanogap NG may be formed to have a length of 2 nm or less. The length of the nanogap NG may denote a distance between the two parts of the first nanogap electrode 170 that may be separated by the nanogap NG.

Although the nanopore NP and the nanogap NG may have the same size in FIG. 1, this is only an example, and the nanopore NP may have a larger diameter than the nanogap NG. The nanogap NG may be formed using FIB equipment.

A protection layer 180 may be formed on the first nanogap electrode 170. The protection layer 180 may be formed of an insulation material.

Figure 3:
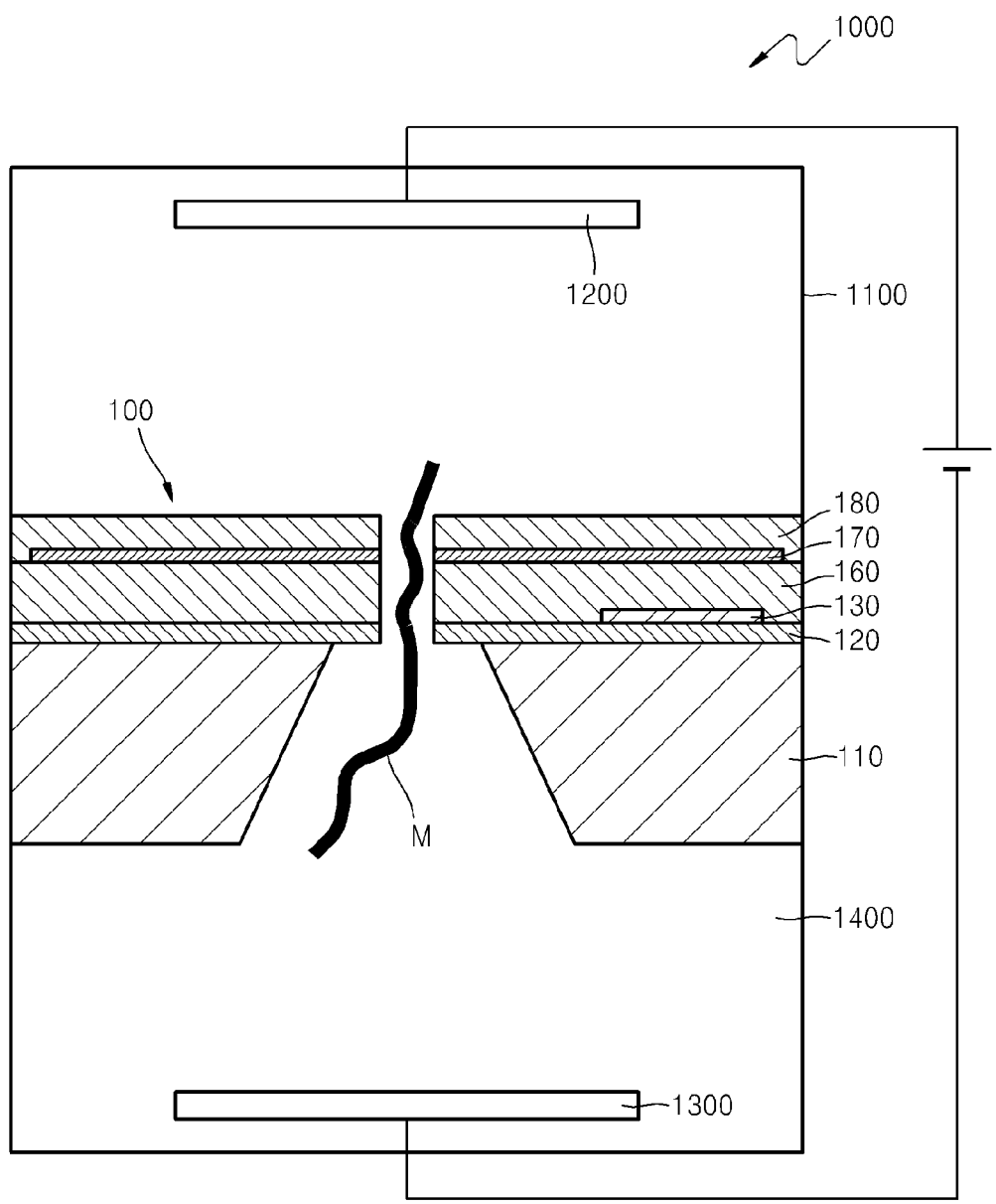
FIG. 3 is a cross-sectional view of a molecule detection apparatus using the nanogap device of FIG. 1, according to example embodiments.

FIG. 3 is a cross-sectional view of a molecule detection apparatus 1000 using the nanogap device 100 of FIG. 1, according to example embodiments.

The molecule detection apparatus 1000 may include the nanogap device 100 of FIG. 1, a water tank 1100 which may contain a sample that may pass through a nanogap, and a first electrode 1200 and a second electrode 1300 which may induce movement of the sample. The molecule detection apparatus 1000 may have, for example, a channel structure that may enable a target molecule M within the sample to flow.

The nanogap device 100 may be disposed within the water tank 1100, and the first electrode 1200 and the second electrode 1300 may be respectively disposed in regions over and under the nanogap device 100 to form an electric field within the sample in order to move the target molecule M within the sample. The water tank 1100 may be filled with a buffer solution, such as, water, deionized water, or an electrolyte solution. The buffer solution may be a movement medium for a target molecule that the nanogap device 100 is to detect. A single strand of DNA, for example, has a negative charge When a voltage is applied from an external power source to the first and second electrodes 1200 and 1300, the DNA may move from a region where the second electrode 1300, namely, a negative electrode, may be located to a region where the first electrode 1200, namely, a positive electrode, may be located, due to an electric field generated by the applied voltage. In other words, the single strand of DNA introduced into the region where the second electrode 1300 may be located may be moved near the hole H of the substrate 110 by the electric field applied thereon, and may be guided toward the nanopore NP by the hole H. When the single strand of DNA passes through the nanogap NG via the nanopore NP, an electrical signal change in the first nanogap electrode 170 may be measured, and thus the bases of the DNA may be distinguished from one another.

Various other channel structures that may enable the target molecule M to pass through the nanogap NG may be used.

Figure 4:
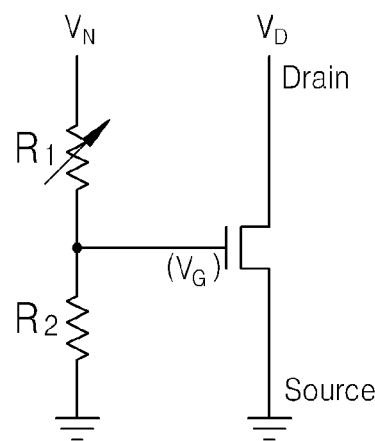
FIG. 4 is a circuit diagram of an equivalent circuit of the nanogap device of FIG. 1.
Figure 5:
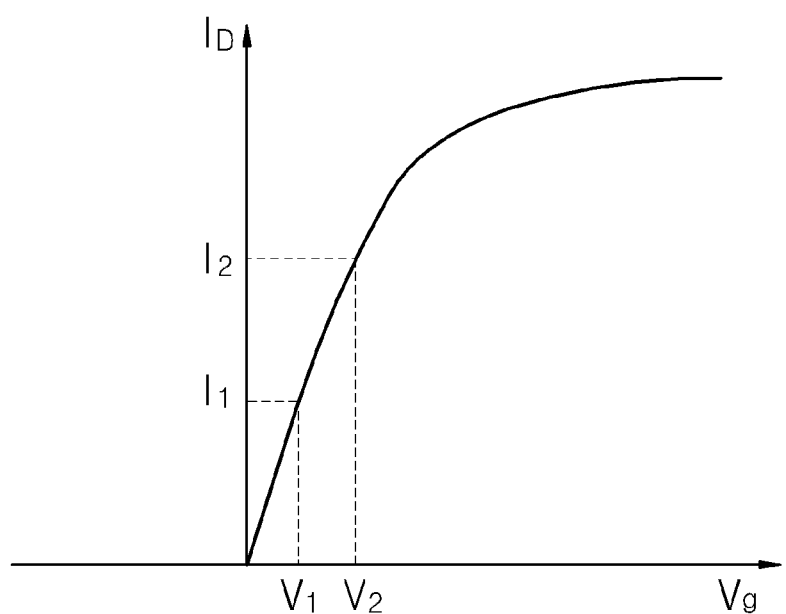
FIG. 5 is a graph showing a drain current versus a voltage of a nanogap electrode that may vary according to a molecule which may pass through a nanogap of the nanogap device of FIG. 1.

FIG. 4 is a circuit diagram of an equivalent circuit of the nanogap device 100 of FIG. 1, and FIG. 5 is a graph showing a drain current ID versus a voltage of the first nanogap electrode 170 that may vary according to a molecule that may pass through the nanogap NG of the nanogap device 100 of FIG. 1.

In the equivalent circuit of FIG. 4, a variable resistance may be caused by the target molecule M that passes through the nanogap NG. The value of the variable resistance may vary depending on the type of base that may be included in the target molecule M, and a gate voltage $V_g$ may vary accordingly. The gate voltage $V_g$, varying as described above, may be detected as an amplified drain current signal, namely, the drain current $I_D$, as illustrated in FIG. 5.

Figure 6:
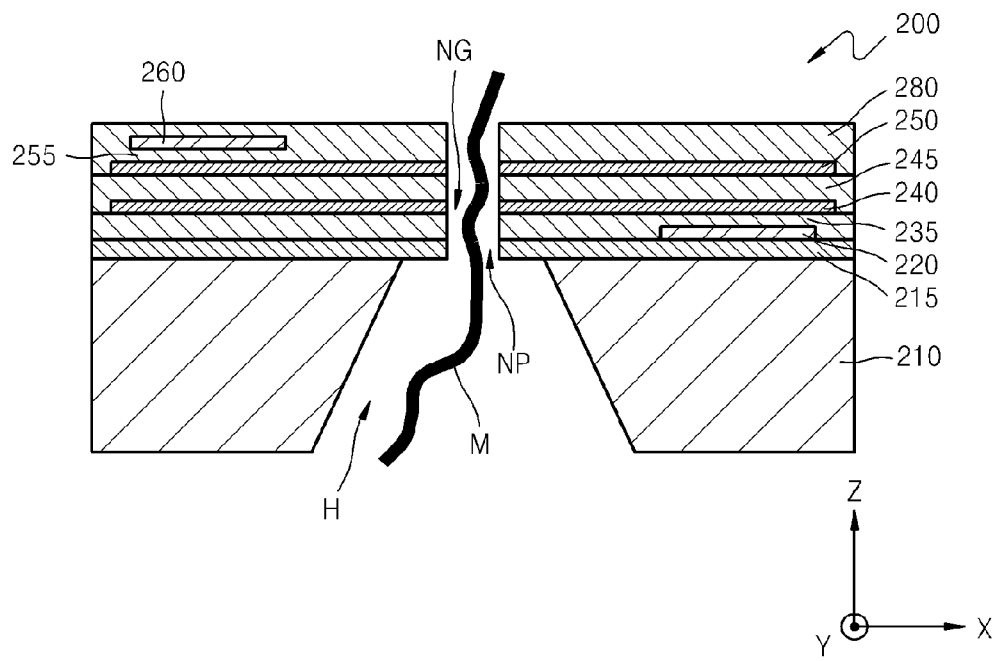
FIG. 6 is a cross-sectional view of a nanogap device according to example embodiments.
Figure 7:
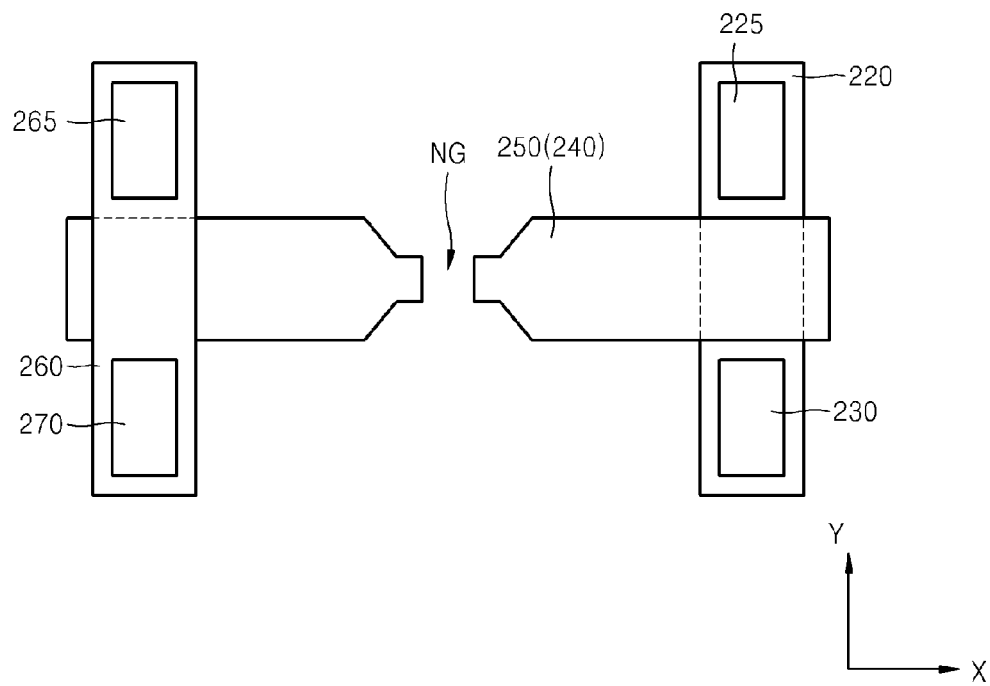
FIG. 7 is a plan view of an arrangement of a first nanogap electrode, a second nanogap electrode, a first drain electrode, a second drain electrode, a first source electrode, and a second source electrode of the nanogap device of FIG. 6.

FIG. 6 is a cross-sectional view of a nanogap device 200 according to example embodiments, and FIG. 7 is a plan view of an arrangement of a first nanogap electrode 240, a second nanogap electrode 250, a first drain electrode 225, a second drain electrode 265, a first source electrode 230, and a second source electrode 270 of the nanogap device 200 of FIG. 6.

Referring to FIGS. 6 and 7, the nanogap device 200 may include a substrate 210 having a hole H, a first insulation layer 215 which may be formed on the substrate 210 and having a nanopore NP, a first channel layer 220 which may be formed on the first insulation layer 215, the first drain electrode 225 and a first source electrode 230 respectively may be formed on both ends of the first channel layer 220 to contact the both ends, a second insulation layer 235 that may cover the first channel layer 220, the first drain electrode 225, and the first source electrode 230, and the first nanogap electrode 240 that may be formed on the second insulation layer 235 and may include two parts separated by a nanogap NG that faces the nanopore NP. The nanogap device 200 may further include a first protection layer 245 which may be formed on a first nanogap electrode 240, the second nanogap electrode 250 which may be formed on the first protection layer 245 and may include two parts separated by the nanogap NG, a third insulation layer 255 which may be formed on the second nanogap electrode 250, a second channel layer 260 which may be formed on the third insulation layer 255, the second drain electrode 265 and a second source electrode 270 which may be respectively formed on both ends of the second channel layer 260 to contact the both ends, and a second protection layer 280 that covers the second channel layer 260, the second drain electrode 265, and the second source electrode 270 and may be formed of an insulation material.

The nanogap device 200 according to example embodiments may be obtained by adding the second nanogap electrode 250 and the second channel layer 260 to the nanogap device 100 of FIG. 1, and the second nanogap electrode 250 may serve as a gate electrode with respect to the second channel layer 260.

The first nanogap electrode 240, the first channel layer 220, the first drain electrode 225, the first source electrode 230, the first insulation layer 215, and the second insulation layer 235 may be substantially the same as the elements having identical names in FIG. 1, so a detailed description thereof is omitted. The structures and materials of the second nanogap electrode 250, the second channel layer 260, the second drain electrode 265, the second source electrode 270, and/or the third insulation layer 255 may be selected from the above-exemplified structures and materials of the first nanogap electrode 170, the first channel layer 130, the first drain electrode 140, the first source electrode 150, and/or the second insulation layer 160 of FIG. 1, respectively.

A drain current $I_D$ may be repeatedly obtained from the nanogap device 200, with a time delay corresponding to a distance between the first nanogap electrode 240 and the second nanogap electrode 250.

Figure 8A:
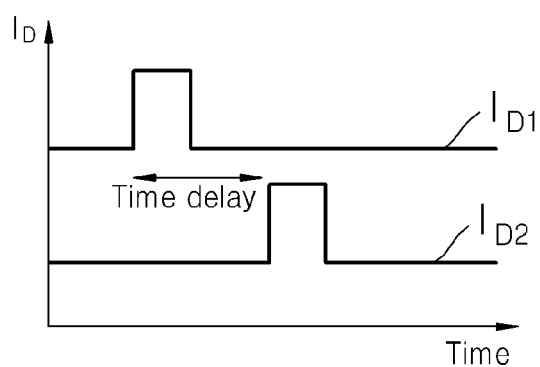
FIGS. 8A and 8B are drain current graphs for describing a method of analyzing a signal from the nanogap device of FIG. 7.
Figure 8B:
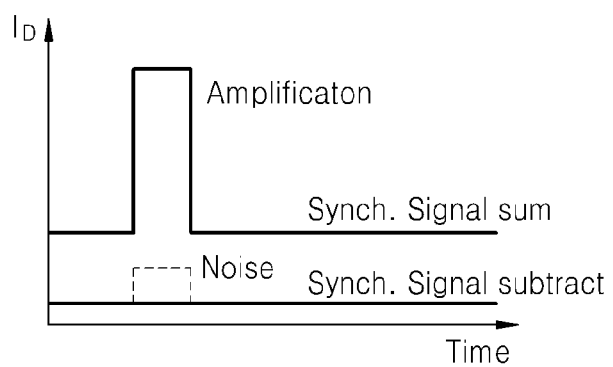

FIGS. 8A and 8B are drain current graphs for describing a method of analyzing a signal from the nanogap device 200 of FIG. 6.

Referring to FIG. 8A, a first drain current signal $I_{D1}$ between the first drain electrode 225 and the first source electrode 230 and a second drain current signal $I_{D2}$ between the second drain electrode 265 and the second source electrode 270 may be measured over time.

The first drain current signal $I_{D1}$ and the second drain current signal $I_{D2}$ may be synchronized with each other and may be used in signal amplification or detection of an error signal. For example, as illustrated in FIG. 8B, an amplification signal Amplification may be obtained from a signal of Synch. Signal sum. The signal of Synch. Signal sum may correspond to a sum of the first drain current signal $I_{D1}$ and the second drain current signal $I_{D2}$ that may be synchronized with each other. An error signal Noise may be obtained from a signal of Synch. Signal subtract. The signal of Synch. Signal subtract may correspond to a difference between the first drain current signal $I_{D1}$ and the second drain current signal $I_{D2}$ that may be synchronized with each other.

Figure 10:
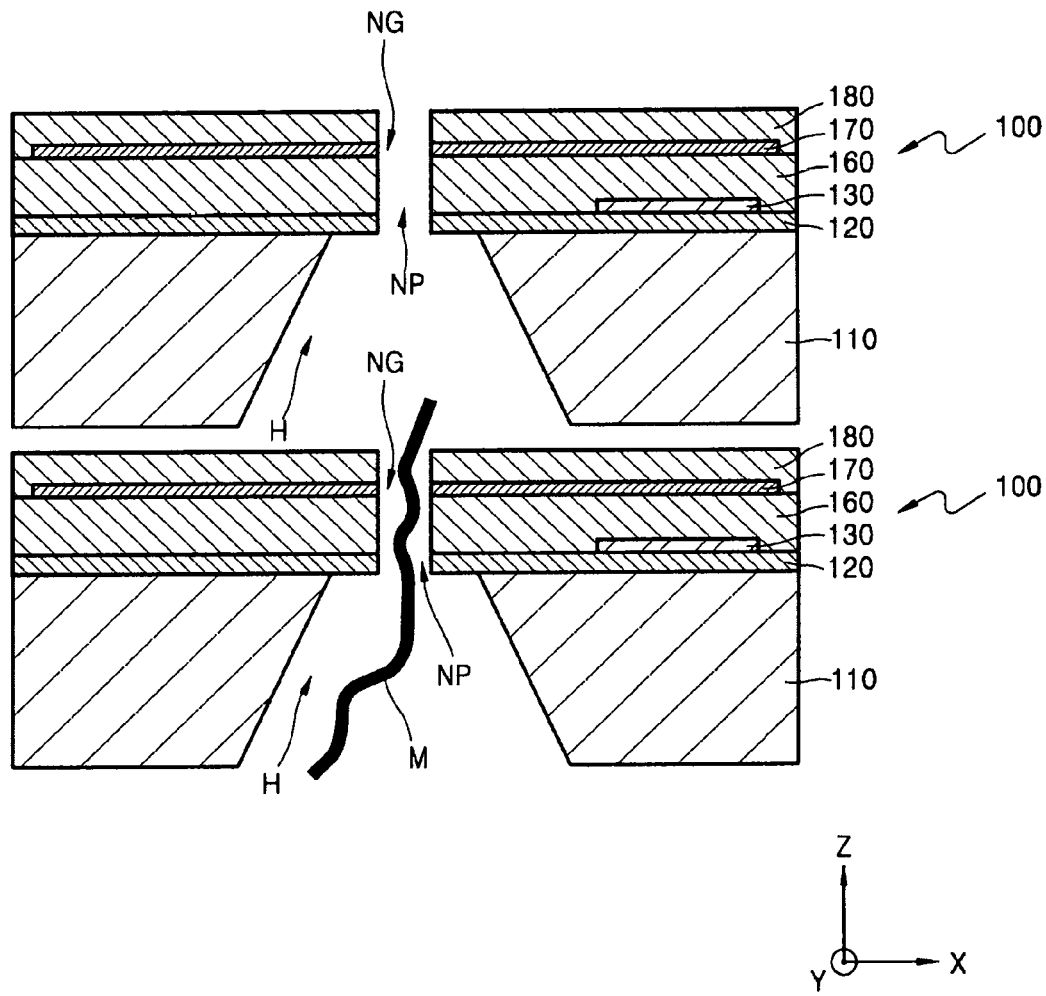
FIG. 10 shows an example that a plurality of the nanogap devices of FIG. 1 is arranged such that respective nanogaps of the plurality of nanogap devices face one another.

Although this signal processing has been described above by referring to the structure of the nanogap device 200 of FIG. 6, the signal processing may be performed with a plurality of nanogap devices 100 of FIG. 1 arranged so that their respective nanogaps NG face each other as is shown in FIG. 10. In other words, a drain current signal between the first drain electrode 140 and the first source electrode 150 of each of the nanogap devices 100 may be measured over time, the respective drain current signals of the nanogap devices 100 may be synchronized with each other, and then an amplification signal or an error signal may be obtained using a sum of or a difference between the synchronized drain current signals.

FIGS. 9A through 9I are cross-sectional views for explaining a method of manufacturing a nanogap device 300, according to example embodiments.

Figure 9A:
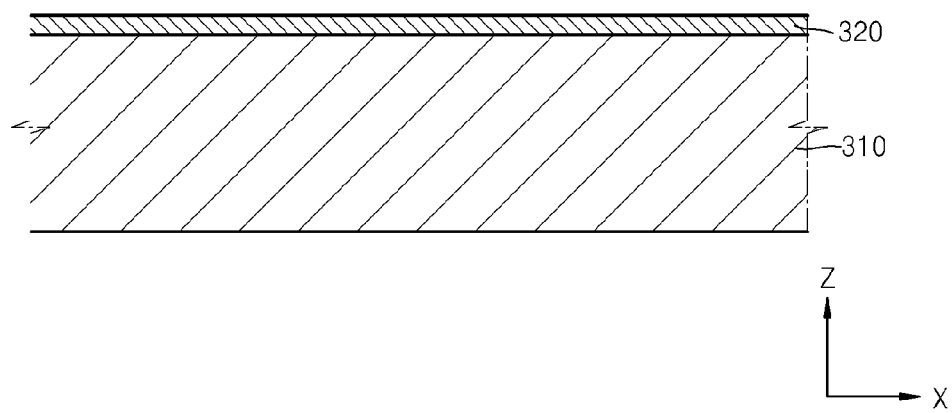
FIGS. 9A through 9I are cross-sectional views for explaining a method of manufacturing a nanogap device, according to example embodiments.

Referring to FIG. 9A, a first insulation layer 320 may be formed on a substrate 310. Semiconductor substrates or polymer substrates formed of various materials may be used as the substrate 310. For example, a silicon substrate may be polished by chemical mechanical polishing (CMP) or the like to have a thickness of about 300 um to thereby form the substrate 310. Although not illustrated in FIGS. 9A through 9I, an etch mask layer for forming a predetermined hole may be further formed on a lower surface of the substrate 310. The first insulation layer 320 may be formed of an insulation material, for example, silicon nitride or silicon oxide, by deposition or the like.

Figure 9B:
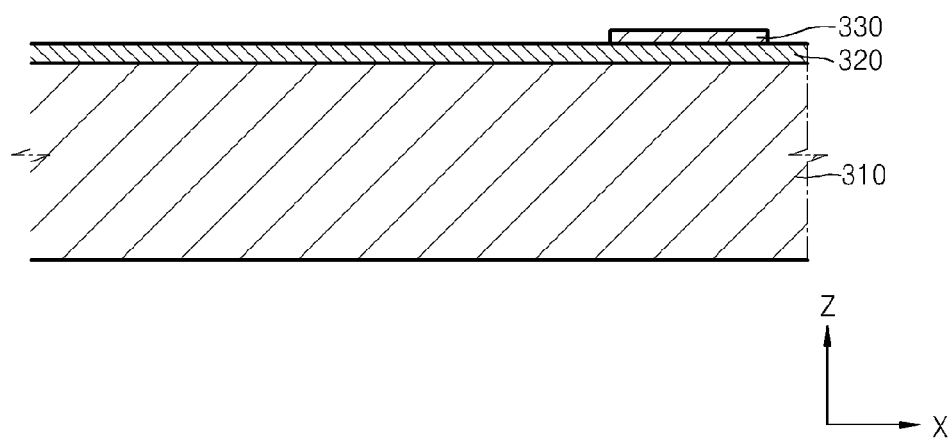

Next, as illustrated in FIG. 9B, a first channel layer 330 may be formed on the first insulation layer 320. The first channel layer 330 may be formed of any of various sorts of semiconductor materials. For example, the first channel layer 330 may be formed of Si, Ge, a compound semiconductor, such as GaAs or GaN, or an oxide semiconductor, such as zinc oxide (ZnO), indium (InO), tin oxide (SnO), indium zinc oxide (InZnO), zinc tin oxide (ZnSnO), or indium tin oxide (InSnO).

Figure 9C:
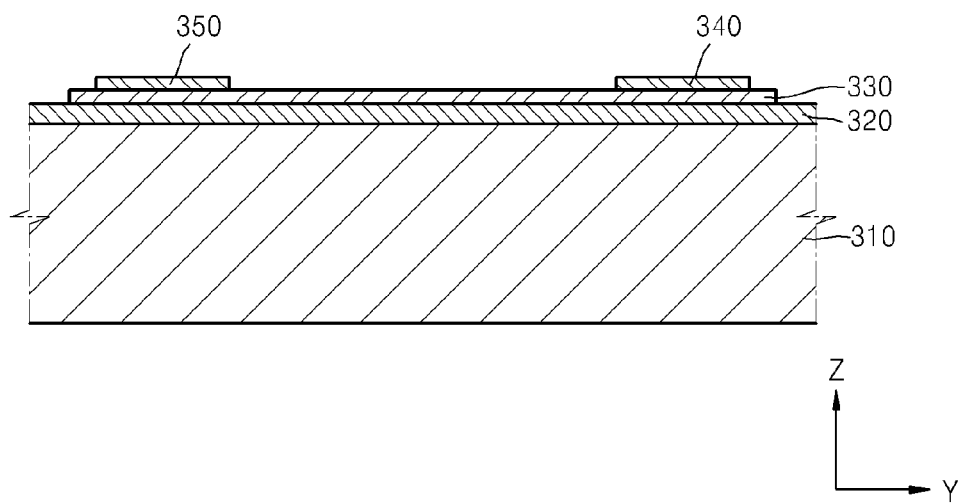
Figure 9D:
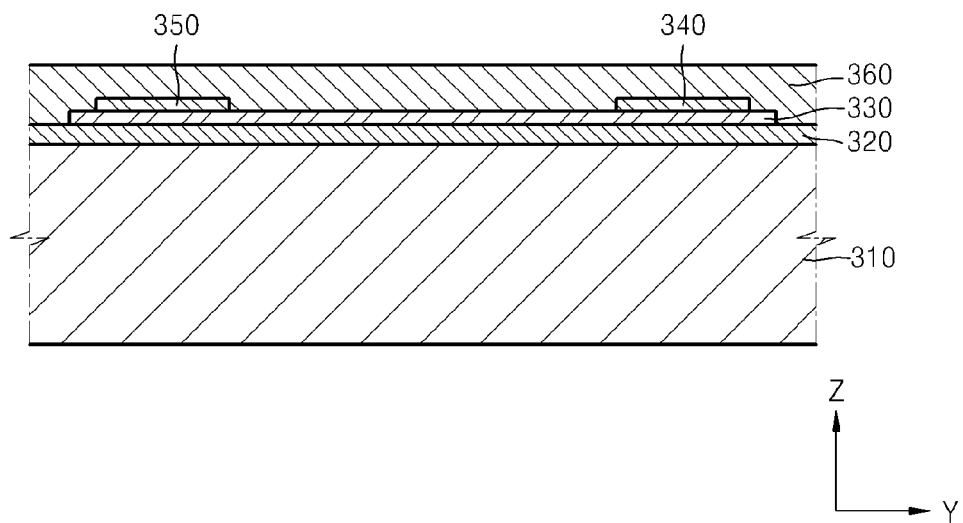

Then, a first drain electrode 340 and a first source electrode 350 respectively contacting both ends of the first channel layer 330 may be formed as illustrated in FIG. 9C, and a second insulation layer 360 that may cover the first channel layer 330, the first drain electrode 340, and the first source electrode 350 may be formed as illustrated in FIG. 9D. The cross-sectional views of FIGS. 9C and 9D are different from the cross-sectional view of FIG. 9B.

The first drain electrode 340 and the first source electrode 350 may be formed by depositing a metal material having high electrical conductivity, for example, platinum (Pt), ruthenium (Ru), gold (Au), silver (Ag), molybdenum (Mo), aluminum (Al), tungsten (W), or copper (Cu). The second insulation layer 360 may be formed of an insulation material, for example, silicon nitride or silicon oxide, by deposition or the like.

Figure 9E:
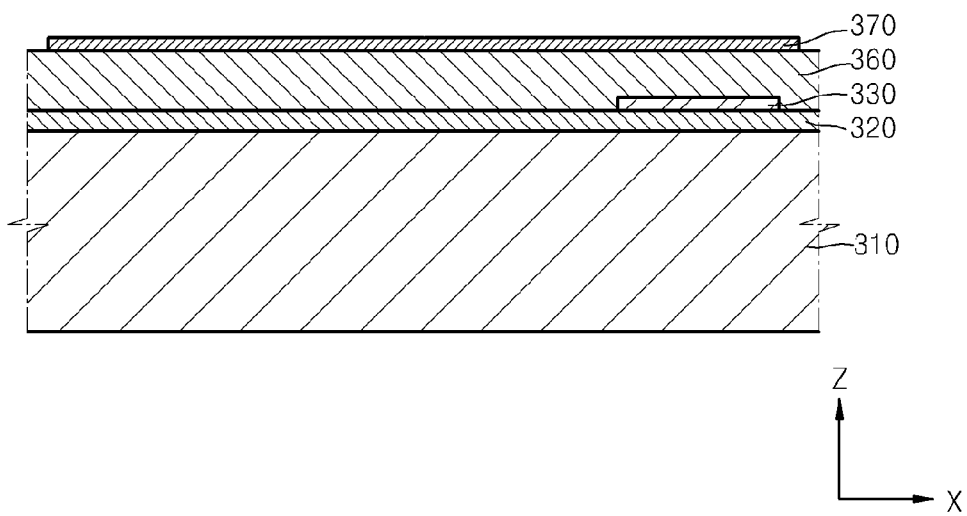
Figure 9F:
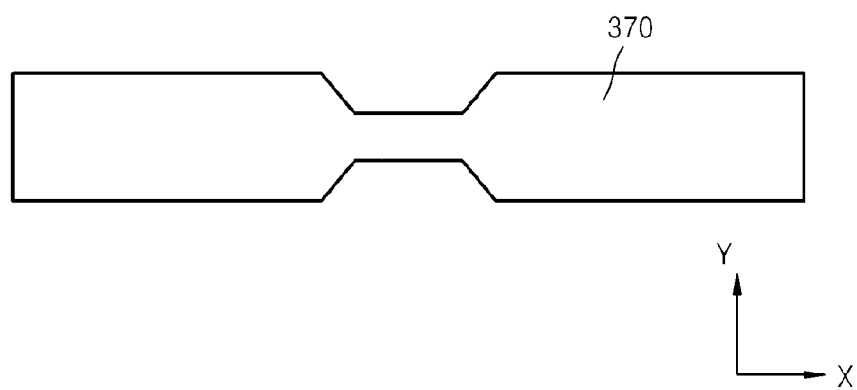

Next, as illustrated in FIG. 9E, a first nanogap electrode 370 may be formed on the second insulation layer 360. The first nanogap electrode 370 may be patterned to have a shape as illustrated in FIG. 9F. The first nanogap electrode 370 may be formed of a metal material or a graphene material.

Figure 9G:
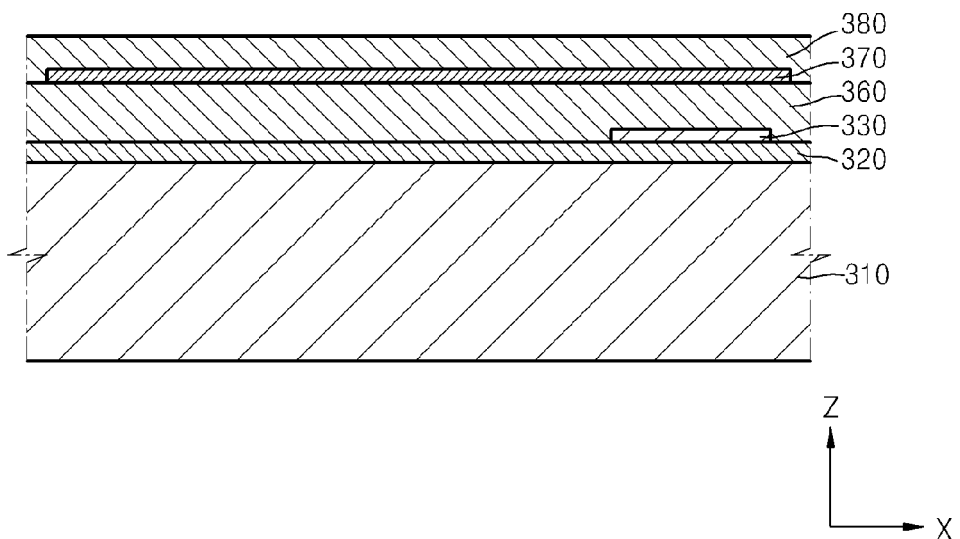

Thereafter, as illustrated in FIG. 9G, a protection layer 380 that may cover the first nanogap electrode 370 may be formed.

Figure 9H:
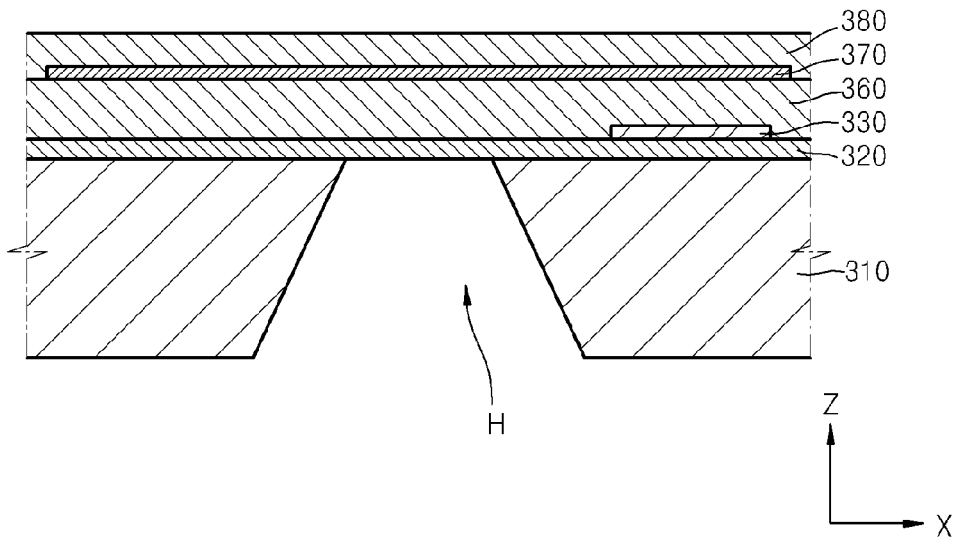

Then, as illustrated in FIG. 9H, the lower surface of the substrate 310 may be anisotropically etched to form a hole H.

Figure 9I:
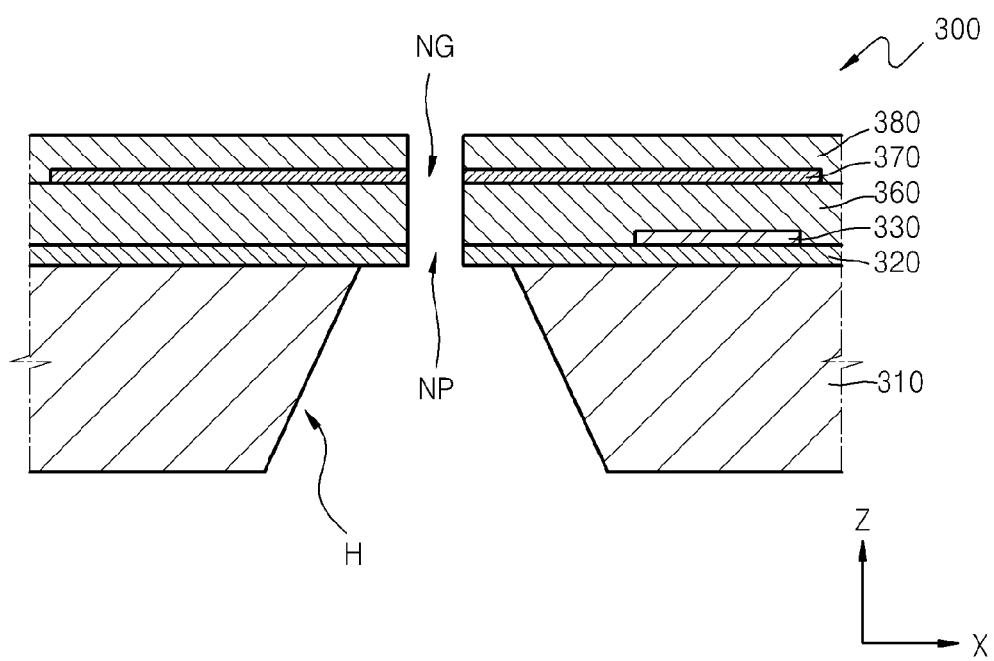

Next, as illustrated in FIG. 9I, a nanopore NP and a nanogap NG may be formed to communicate with the hole H, by using FIB equipment or transmission electron microscope (TEM) equipment. Although the nanopore NP and the nanogap NG may have the same size in FIG. 9I, this is only an example, and the nanopore NP may be larger than the nanogap NG.

Although FIG. 9I illustrates that the nanogap device 300 manufactured in this way has a similar structure to the nanogap device 100 of FIG. 1, the nanogap device 300 may be manufactured to include two layers of nanogap electrodes as illustrated in FIG. 6 by repeating similar process operations.

Since a nanogap device as described above may have a structure that enables a nanogap electrode to be used as a gate electrode of a transistor, a small electrical signal in the nanogap electrode may be amplified.

Alternatively, the nanogap device as described above may have a structure including two layers of nanogap electrodes and two channel layers, and two signals may be obtained from this structure and may be used in base analysis.

According to a method of processing a signal from a nanogap device as described above, repetitive measurements may be performed on the same base at regular intervals, and the results of the measurements may be synchronized with each other to obtain an amplification signal or an error signal.

It should be understood that example embodiments having thus been described should be considered in a descriptive sense only and not for purposes of limitation. Descriptions of features or aspects within each nanogap device according to example embodiments should typically be considered as available for other similar features or aspects in other nanogap devices according to example embodiments. For example, one skilled in the art knows that the structure of a nanogap device, a signal processing method using the nanogap device, and a method of manufacturing the nanogap device shown in FIGS. 1 through 9I may be variously modified. Therefore, while some example embodiments have been particularly shown and described, it will be understood by one of ordinary skill in the art that variations in form and detail may be made therein are not to be regarded as a departure from the intended spirit and scope of example embodiments, and all such modifications as would be obvious to one skilled in the art are intended to be included within the scope of the following claims.

What is claimed is:

1. A nanogap device comprising:
   a first insulation layer having a nanopore therein;
   a first channel layer on the first insulation layer;
   a first source electrode and a first drain electrode respectively in contact with both ends of the first channel layer;
   a second insulation layer covering the first channel layer, the first source electrode, and the first drain electrode; and
   a first nanogap electrode on the second insulation layer and divided into a first part and a second part arranged in a first direction and spaced apart from each other by a nanogap, the nanogap facing the nanopore,
   wherein the first source electrode and the first drain electrode face the first part of the first nanogap electrode, and are arranged along a second direction different from the first direction.

2. The nanogap device of claim 1, wherein the first part of the first nanogap electrode serves as a gate electrode with respect to the first channel layer.

3. The nanogap device of claim 1, wherein a first portion of the first part and a first portion of the second part of the first nanogap electrode that face the nanogap are narrower than a second portion of the first part and a second portion of the second part, respectively.

4. The nanogap device of claim 1, wherein a thickness of the first nanogap electrode is 1 nm or less.

5. The nanogap device of claim 1, wherein a length of the nanogap of the first nanogap electrode is 2 nm or less.

6. The nanogap device of claim 1, wherein the first nanogap electrode includes a graphene material.

7. The nanogap device of claim 1, further comprising:
   a substrate having a hole formed therein,
   wherein the first insulation layer is on the substrate so that the nanopore faces the hole of the substrate.

8. The nanogap device of claim 7, wherein the hole has an inclined side surface and narrows from an entrance to an inside of the hole.

9. A method of processing a signal from a nanogap device, the method comprising:
arranging a plurality of the nanogap devices of claim 1 such that respective nanogaps of the plurality of nanogap devices face one another;
measuring a drain current signal between the first drain electrode and the first source electrode of each of the plurality of nanogap devices according to time; and
synchronizing the respective drain current signals of the plurality of nanogap devices with one another.

10. The method of claim 9, further comprising:
summing the synchronized drain current signals of the plurality of nanogap devices to obtain an amplification signal.

11. The method of claim 9, further comprising:
obtaining an error signal from a difference between the synchronized drain current signals of the plurality of nanogap devices.

12. A nanogap device comprising:
a first insulation layer having a nanopore therein;
a first channel layer on the first insulation layer;
a first source electrode in contact with a first end of the first channel layer and a first drain electrode in contact with a second end of the first channel layer;
a second insulation layer covering the first channel layer, the first source electrode, and the first drain electrode;
a first nanogap electrode on the second insulation layer and divided into two parts by a nanogap, the nanogap facing the nanopore;
a first protection layer on the first nanogap electrode;
a second nanogap electrode on the first protection layer and divided into two parts by a nanogap, the nanogap facing the nanopore;
a third insulation layer on the second nanogap electrode;
a second channel layer on the third insulation layer; and
a second source electrode in contact with a first end of the second channel layer and a second drain electrode in contact with a second end of the second channel layer.

13. The nanogap device of claim 12, wherein the second nanogap electrode acts as a gate electrode with respect to the second channel layer.

14. The nanogap device of claim 13, further comprising:
a second protection layer covering the second channel layer, the second drain electrode, and the second source electrode.

15. The nanogap device of claim 13, wherein portions of the two parts of the second nanogap electrode that face the nanogap are narrower than other portions of the two parts.

16. The nanogap device of claim 13, wherein a thickness of the second nanogap electrode is 1 nm or less.

17. The nanogap device of claim 13, wherein a length of the nanogap of the second nanogap electrode is 2 nm or less.

18. The nanogap device of claim 12, wherein the second nanogap electrode includes a graphene material.

19. A method of processing a signal from the nanogap device of claim 12, the method comprising:
measuring a first drain current signal between the first drain electrode and the first source electrode according to time; and
measuring a second drain current signal between the second drain electrode and the second source electrode according to time.

20. The method of claim 19, further comprising:
synchronizing the first drain current signal with the second drain current signal.

21. The method of claim 20, further comprising:
obtaining an amplification signal from a sum of the synchronized first and second drain current signals.

22. The method of claim 20, further comprising:
obtaining an error signal from a difference between the synchronized first and second drain current signals.

\* \* \* \* \*